US006692921B1

(12) United States Patent
Horton et al.

(10) Patent No.: US 6,692,921 B1
(45) Date of Patent: Feb. 17, 2004

(54) METHOD FOR MEASUREMENT OF TOTAL ANALYTE

(75) Inventors: Jeffrey Horton, Wyndham Park (GB); Peter Baxendale, South Glamorgan (GB)

(73) Assignee: Amersham Biosciences UK Limited, Amersham (GB)

( * ) Notice: Subject to any disclaimer, the term of this patent is extended or adjusted under 35 U.S.C. 154(b) by 0 days.

(21) Appl. No.: 09/622,106

(22) PCT Filed: Feb. 15, 1999

(86) PCT No.: PCT/GB99/00515

§ 371 (c)(1),
(2), (4) Date: Oct. 13, 2000

(87) PCT Pub. No.: WO99/41609

PCT Pub. Date: Aug. 19, 1999

(30) Foreign Application Priority Data

Feb. 16, 1998 (GB) ............................................ 98301126

(51) Int. Cl.[7] ...................... G01N 33/53; G01N 33/543
(52) U.S. Cl. ..................... 435/7.1; 435/7.2; 435/7.8; 435/7.9; 435/174; 435/180; 436/501; 436/518; 436/523; 436/524; 436/533; 436/534; 436/536
(58) Field of Search ................................. 436/501, 523, 436/524, 533, 534, 536, 518; 435/7.1, 7.2, 7.8, 7.9, 174, 180

(56) References Cited

U.S. PATENT DOCUMENTS 5,516,647 A * 5/1996 Husain et al. ................. 435/21
5,558,986 A * 9/1996 Lundin ........................... 435/4
5,646,005 A * 7/1997 Kudsk ....................... 435/7.32
5,705,345 A * 1/1998 Lundin et al. .................. 435/6

FOREIGN PATENT DOCUMENTS

| EP | 0301847 | * | 7/1988 | ............ C11D/3/00 |
| EP | 0348173 | * | 7/1989 | .................... 33/53 |
| WO | 9212253 | * | 7/1992 | |

OTHER PUBLICATIONS

Park et al Archives of biochemistry and biophysics Aug. 15, 1984 233 1 290–8.*
Nelson Analytical Biochem 165, 287–293 (1987).*

* cited by examiner

Primary Examiner—Long V. Le
Assistant Examiner—Kartic Padmanabhan
(74) Attorney, Agent, or Firm—Stephen G. Ryan; Royal N. Ronning, Jr.; Yonggang J.

(57) ABSTRACT

A method of assaying for an analyte which occurs at least partially bound as a complex with its soluble receptor or binding protein, the method comprising the steps of:

i) mixing a biological fluid serum sample containing the analyte to be determined with a detergent for dissociating said complex, ii) mixing the sample from step i) with reagents, including a specific binding partner of the analyte for binding to the analyte, for performing a specific binding assay for the analyte, iii) and mixing the sample from step i) with a sequestrant for the detergent, whereby the binding of step ii) is performed in the presence of the sequestrant.

9 Claims, 3 Drawing Sheets

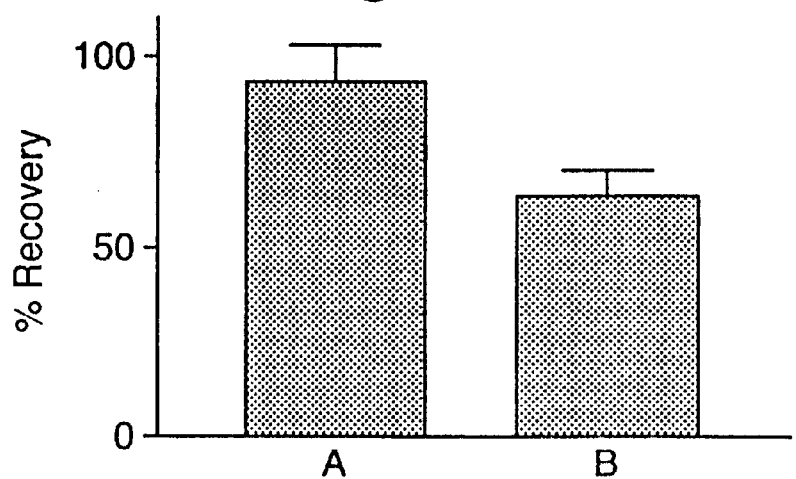
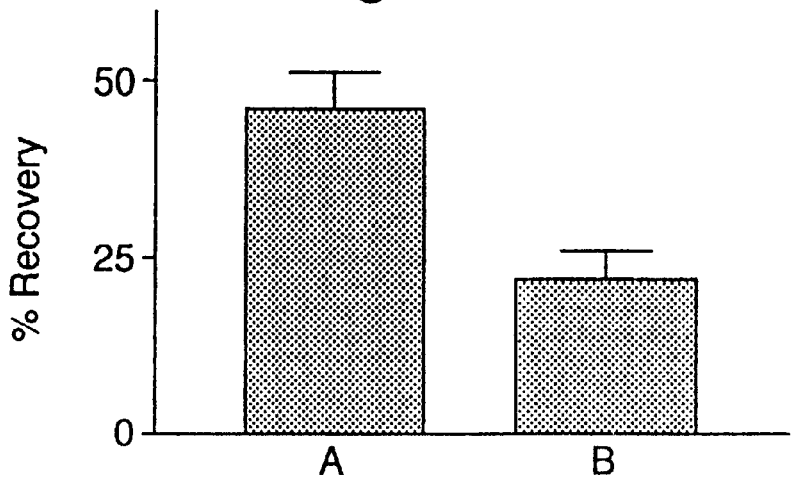

METHOD FOR MEASUREMENT OF TOTAL ANALYTE

FIELD OF THE INVENTION

A The present invention relates to the field of immunoassays. The invention provides a simple and convenient method suitable for the measurement of a range of different types of analyte which occur, either totally or partially complexed with soluble binding proteins or receptors, in serum or plasma. The invention also relates to kits of reagents suitable for performing measurements of analytes using separation-based or homogeneous immunoassays.

BACKGROUND OF THE INVENTION

For more than thirty years, immunoassays have been the method of choice for measuring low analyte concentrations in complex biological fluids. The procedure is equally applicable to the measurement is of low molecular weight compounds such as drugs, steroids and the like, as well as large molecular weight compounds such as protein molecules. The technique combines sensitivity and specificity and have been used in basic biological research to investigate the physiological and possible pathological role of a wide range of potent biologically active substances, including cytokines, steroid hormones, cyclic nucleotides, prostaglandins, leukotrienes and growth factors. Assay designs have proliferated over the last thirty years, as have the different types of signal reagents and detection systems. Sophisticated instruments with associated computer hardware have been developed with the aim of increasing sample throughput. Further background information relating to immunoassay techniques can be found in 'The Immunoassay Handbook', (Wild, D. G. Ed, Stockton Press, New York, [1994]).

The earliest methods were those which involved a step of separating the bound analyte from the free, in order to be able to measure the amount of bound analyte. Various separation methods have been described, including charcoal absorption, ammonium sulphate precipitation. More recently, solid supports have been utilised for immunoassay procedures, including magnetic particles and the walls of microtitre well plates. A recent development has been the introduction of homogeneous radioimmunoassay technology, e.g. the technique of scintillation proximity assays (SPA) covered by U.S. Pat. No. 4,568,649.

As an alternative to radioisotopically-based immunoassay methods, non-radioactive systems have been introduced. Today, enzymes are the most widely used tracers in such immunoassay systems as ELISAs and EIAs. When used in combination with colourimetric end-points, they provide highly sensitive, robust, precise, accurate and convenient immunoassays. A major breakthrough came with the introduction of ninety-six well microtitre plates. Inexpensive automatic colourimetric multiwell plate readers are available. A number of other non-isotopic labels have been described, of which luminescent and fluorescent labels are the most popular.

Despite the widespread use of immunoassays, there are still difficulties in the measurement of analytes derived from particular sample types, notably plasma and serum, in which the analyte may be totally or partially complexed with a soluble receptor or binding protein. Engelberts et al (The Lancet, 338, 515∝6, 1991) have compared the results of the measurement of TNFα in plasma samples from septic shock patients using a range of assay types and have noted a marked variation in the amount of TNF detected. In this context, it has been suggested that TNF binding proteins present in biological fluids prevent the biological activity of TNF and cause discrepancies between various assay measurements. The difficulty in measuring analytes in the form of their complexes with soluble receptors or binding proteins, may be due to the masking of antibody binding sites.

This problem has been addressed previously by the development of an "oligoclonal" assay system (Medgenix), in which up to three non-neutralising monoclonal antibodies are used in a standard ELISA assay for the measurement of cytokines. In this assay format, monoclonal antibodies are selected to recognise epitopes which are recognisably different from the binding site of the receptor or binding protein. As a result the assay is claimed to suffer no interference from soluble receptors or inhibitors and is capable of measuring total cytokine.

U.S. Pat. No. 4,121,975 (Ullman and Lavine) describes a method for pre-treatment of serum samples prior to the determination by immunoassay of polyiodothyronine, particularly thyroxine. In this assay, alkaline salicylate is added to serum as an agent to release thyroxine from its binding protein. Alpha-cyclodextrin is also included in the serum sample to complex naturally occurring, endogenous interfering molecules such as free fatty acids, lipids, and drugs. Cyclodextrin was not added to serum to sequester the salicylate or to safeguard the antibody components of the immunoassay. Moreover, the method is described for use with only one analyte.

U.S. Pat. No. 4,798,804 (Khanna and Pearlman) describe a method for serum pre-treatment prior to digoxin immunoassay. The method comprises contacting the serum sample to be analysed with β-cyclodextrin or β-cyclodextrin polymer in an amount and under conditions sufficient to allow a substantial portion of digoxin in the sample to bind to the β-cyclodextrin. The β-cyclodextrin-digoxin complex is separated from the other components of the medium by filtration or centrifugation, and the digoxin from the sample is thus highly concentrated. The digoxin is released from the β-cyclodextrin complex using cyclohexanol to provide a digoxin sample which may be analysed by a number of immunoassay techniques.

SUMMARY OF THE INVENTION

In view of the needs of the prior art, the present invention provides a method of assaying for an analyte which occurs at least partially bound as a complex with its soluble receptor or binding protein. The method includes the step of forming a fluid mixture by mixing a biological fluid sample containing the analyte to be determined with a detergent for dissociating the complex. The method also includes mixing the fluid mixture obtained from the forming step with reagents, including a specific binding partner of the analyte for binding to the analyte, and performing a specific binding assay for the analyte. The method further includes the step of mixing the fluid mixture obtained from the forming step with a sequestrant and a detergent, whereby the specific binding assay of the mixing step is performed in the presence of the sequestrant. The present invention also provides a kit adaptable for performing the method of the present invention.

BRIEF DESCRIPTION OF THE FIGURES

FIG. 1 depicts the inhibition of binding in the IL-6 ELISA with detergent whereby Interleukin-6 standards (10.24–400 pg/ml) were prepared in standard diluent either in the presence (□) or absence (●) of detergent (1% w/v DTAB). Aliquots (50 µl) of biotinylated antibody (zero cyclodextrin) were added to the anti-IL-6 coated plate followed by standard (50 µl). The plate was incubated for 2 hours at room temperature, and the optical density measured as described hereinbelow.

Figure 2:
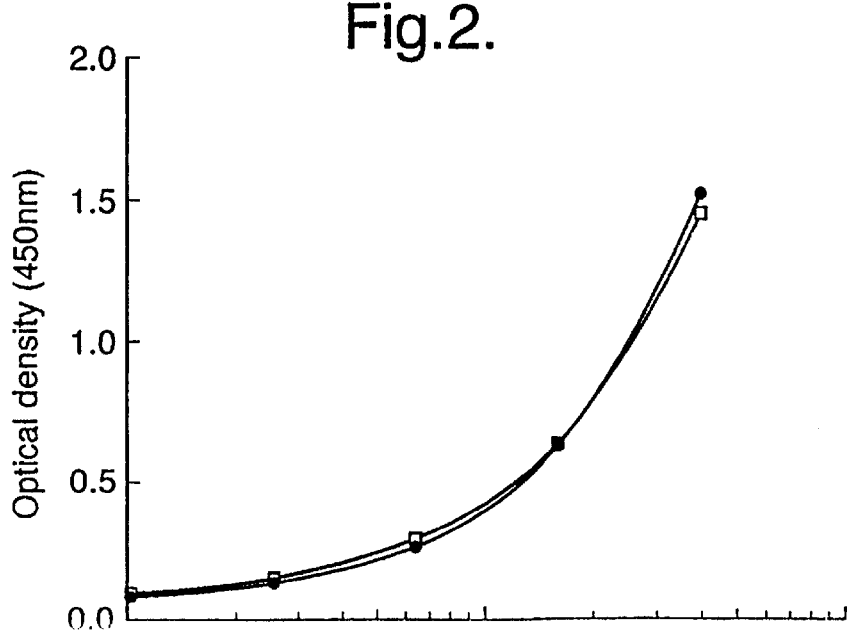

FIG. 2 depicts the restoration of binding in the IL-6 ELISA with cyclodextrin whereby Interleukin-6 (10.24–400 pg/ml) were prepared in standard diluent either in the presence (□) or absence (●) of detergent (1% DTAB). Aliquots (50 µl) of biotinylated antibody, prepared in the presence (□) or absence (●) of cyclodextrin (3% w/v), were added to the anti-IL-6 coated plate followed by standard (50 µl). The plate was incubated for 2 hours at room temperature, and the optical density measured as described hereinbelow.

FIG. 3 depicts recovery of recombinant interleukin-6 from plasma whereby normal human plasma samples were spiked with known concentrations (25–200 pg/ml) of recombinant human interleukin-6. Samples were measured in the presence (A) and absence (B) of detergent and cyclodextrin. A number of different dilutions of plasma were evaluated. Assays were carried out as described hereinbelow.

FIG. 4 depicts recovery of recombinant interleukin-6 from plasma in the presence of soluble IL-6 receptor whereby normal human plasma samples were spiked with known concentrations (25–200 pg/ml) of recombinant human interleukin-6 and soluble IL-6 receptor (12.5 ng/ml). Samples were measured in the presence (A) and absence (B) of detergent and cyclodextrin. A number of different dilutions of plasma were evaluated. Assays were carried out as described hereinbelow.

Figure 5:
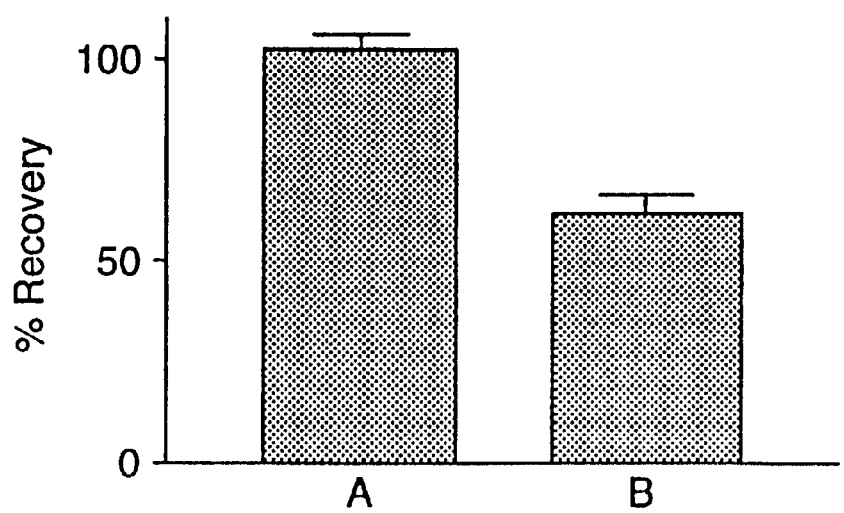

FIG. 5 depicts recovery of $PGE_2$ from plasma whereby normal human plasma samples were spiked with known concentrations (25–200 pg/ml) of $PGE_2$. Samples were measured in the presence (A) and absence (B) of detergent and cyclodextrin. A number of different dilutions of plasma were evaluated. assays were carried out as described hereinbelow.

DETAILED DESCRIPTION OF THE PREFERRED EMBODIMENTS

The present method provides a novel, convenient and rapid method for the quantitation of total analyte in a sample in which the analyte may be partially or totally bound to its soluble receptor or binding protein. The method does not depend on the use of a multi-antibody format, and does not require extensive manipulation of the sample to ensure that the analyte is in a form suitable for measurement. The method described herein combines conventional immunoassay technology with a detergent mediated dissociation of the analyte from its receptor or binding protein.

Accordingly, the present invention provides a method of assaying for an analyte which occurs at least partially bound as a complex with its soluble receptor or binding protein, the method comprising the steps of:
i) mixing a biological fluid sample containing the analyte to be determined with a detergent for dissociating said complex,
ii) mixing the sample from step i) with reagents, including a specific binding partner of the analyte for binding to the analyte, for performing a specific binding assay for the analyte,
iii) and mixing the sample from step i) with a sequestrant for the detergent, whereby the binding of step ii) is performed in the presence of the sequestrant.

The analyte may be a component of a biological fluid. Any analyte for which a specific binding partner is available can in principle be utilised in the invention. Typical specific-binding partner combinations suitable for use with the invention may be selected from: hapten-antibody, drug-antibody, steroid hormone-antibody, protein-antibody, peptide-antibody, and polypeptide-antibody interactions. A specific binding protein preparation may be substituted for an antibody in these systems. Preferably the specific binding assay is a protein-binding assay or particularly an immunoassay. Typical analytes include proteins, peptides, cytokines, chemokines, second messengers such as cyclic AMP and cGMP, hormones, drugs, steroids, prostaglandins, vitamins and leukotrienes.

The assay may be designed to measure an analyte present in a biological fluid sample, for example serum, plasma or amniotic fluid, in which sample the analyte may be totally or partially bound as a complex with its soluble receptor or binding protein. Preferred fluids are serum and plasma.

Suitably, the detergent may be any reagent capable of dissociating an analyte from its complementary receptor or binding protein and may be cationic, anionic, zwitterionic or non-ionic in nature. Examples of suitable detergents include dodecyl trimethyl ammonium bromide (DTAB); cetyl pyridinium chloride (CPC); benzethonium chloride (BZC); sodium dodecyl sulphate (SDS), and N-dodecyl-N,N-dimethyl-3ammonio-1-propane sulphonats (DDAPS). DTAB, CPC and BZC are cationic surfactants; DDAPS is a zwitterionic surfactant and SDS is an anionic surfactant. Typical concentrations of detergent are in the range of 0.25–4%, preferably in the range 0.5–2.5% by weight of the weight of the sample to be determined. If too little detergent is used, then dissociation of the analyte from its soluble receptor or binding protein may be slow or incomplete. In addition to the dissociative activity of the detergent in order to release an analyte suitable for measurement, the detergent may also adversely affect the binding of the analyte to its specific binding partner added in the course of step ii) for assay. The sequestrant is used to inhibit or annul that undesired adverse effect.

A key feature of the invention is the use of a sequestrant for the detergent. The sequestrant acts to prevent the detergent and any associated components bound thereto from adversely affecting a binding reaction between the analyte and its specific binding partner. The sequestrant may do this e.g. by chemically reacting with the detergent or by physically absorbing it. Preferred sequestrants are complex carbohydrate molecules such as cyclodextrins. Cyclodextrins are toroldal molecules consisting of 6, 7 or 8 glucose units (α-, β- and γ-cyclodextrin). The interior of the ring binds a hydrophobic tail of a molecule such as a surfactant. The resultant inclusion complex is generally formed with a 1:1 stoichiometry between surfactant and cyclodextrin. γ-Cyclodextrin and particularly α-cyclodextrin are preferred for use in this invention. Preferably enough sequestrant is used to be capable of sequestering or inactivating all the cell lysis reagent present. Suitably the amount of sequestrant is from 0.5–10%, preferably 1–5%, by weight of the weight of the reaction mixture.

Preferably, multiple stages are performed in sequence in a multiwell plate, such as a microtitre plate, or in assay tubes. If desired, the contents of individual wells of a multiwell plate can be transferred to individual wells of another multiwell plate at any stage during performance of the method. However, it is an advantage of the invention that steps i), ii) and iii) can all preferably be performed in a single reaction vessel using a homogeneous immunoassay.

Preferably, the treated sample that results from step i) is used, without any intermediate separation or purification, for performing steps ii) and iii). Preferably the sequestrant is included in one of the reagents that is mixed with the fluid sample in step ii). Thus the components present in an assay according to the invention may typically comprise:
- a) a sample possibly, or suspected of, containing the analyte;
- b) a detergent;
- c) an unlabelled specific binding partner of the analyte which is, or is capable of being, immobilised on a solid support;
- d) a specific binding partner or an analogue of the analyte, which are either labelled, or unlabelled and capable of being labelled.

One or both of components c) and d) includes a sequestrant, the order of addition of components c) and d) being immaterial.

In one format of the invention, the immunoassay is an enzyme-linked immunosorbent assay (ELISA). In this format, components a), b), c) and d) are contained in the wells of a microtitre well plate, component d) being an enzyme-labelled specific binding partner of the compound being tested for. The assay measurement is initiated by the addition to the wells of detection reagents suitable for the detection of the enzyme label. In an alternative format of the invention, the immunoassay is a radioimmunoassay. In this format, components a), b), c) and d) are contained assay tubes, component d) being a radioactively-labelled analogue of the compound being tested for.

Suitable sequestration reagents are chosen from the group consisting of complex carbohydrates, including cyclodextrins. In a preferred format, alpha-cyclodextrin is employed in the method of this invention.

The method comprises incubating a sample containing or suspected of containing an analyte to be measured with detergent, adding to the mixture the reagents necessary for performing an immunoassay for the measurement of the analyte, one or more such reagents being dissolved in a buffer containing sequestration agent and measuring the signal generated as a measure of the amount of analyte present. The signal obtained may be compared with the signals obtained using a set of standard quantities of analyte using a parallel procedure and generating a standard curve for the assay.

In another aspect the invention provides a kit, for assaying for an analyte by the method described, comprising: a detergent; a sequestrant for the detergent; a specific binding partner of the analyte; a tracer; and separation means for separating bound tracer from unbound tracer. The tracer is a labelled assay reagent which might be the specific binding partner of the analyte or might be another assay reagent. Separation means envisaged include assay reagents which are immobilised e.g. on SPA beads or magnetic beads or on an inner surface of the assay vessel. The kit may also include an analyte standard and a buffer.

In one format, the immunoassay process is a radioimmunoassay, in which the reagent d) is an analogue containing a radioisotope. Suitable radioisotopes for use in the assay method of the present invention include β-emitting isotopes such as tritium, and iodine-125 which emits Auger electrons.

In an alternative format, the immunoassay process is an enzyme-immunoassay, in which reagent d) is a specific binding partner which is, or can be, bound to an enzyme label. Typical enzyme labels suitable for use in the present invention are alkaline phosphatase, β-galactosidase, horseradish peroxidase, malate dehydrogenase and glucose-6-phosphate dehydrogenase. Horseradish peroxidase is a particularly preferred enzyme label for use in the enzyme immunoassay method according to the present invention.

In another format, the labelled specific binding partner can include a fluorescence label. Suitable fluorescent labels for use in the present invention may be selected from fluorescein, rhodamine and cyanine dyes.

The precise assay format, choice of specific binding partner, the detection label, and the nature of the substance to be tested for are not critical to the present invention. Rather, the invention relies on the unexpected observation that an analyte, which may be totally or partially complexed with its soluble binding protein or receptors, may be determined by use of a detergent treatment step in the assay procedure, whereby a sequestration agent is also included to render the analyte in a form suitable for measurement.

Illustrative of the immunoassay methods which can be utilised in the present invention are the following assay formats.

I. RADIOIMMUNOASSAYS i) Heterogeneous (Separation-based)-Radioimmunoassay (RIA)

The present method provides a simple method for measuring analytes which may be totally or partially complexed with soluble binding proteins or receptors. The immunoassay reagents (antisera and tracer) may be added to the same wells as are used for step i) of the process. In the alternative, an aliquot of the sample from step i) may be transferred to individual wells of a second vessel to which are added the immunoassay reagents. The process is thereafter carried out in single wells or tubes without further sample preparation.

A detergent is added to the plasma or serum sample to be measured, followed by unlabelled specific binding partner and a labelled analogue of the analyte, one or both reagents being prepared in buffer containing the sequestration agent. The reagents are incubated together for a suitable time period. The bound labelled analyte-specific binding partner immune-complex is separated from unbound label by conventional means (e.g. charcoal absorption, ammonium sulphate precipitation or magnetic particles), and an aliquot of supernatant or pellet is taken for counting. The concentration of analyte in the samples is determined by interpolation from a standard curve.

ii) Scintillation Proximity RIA

A detergent is added to the plasma or serum sample, followed by labelled specific binding partner, unlabelled binding partner and second antibody derivatised scintillant beads prepared in buffer containing the sequestration agent. The immunoassay reagents (antisera, tracer, SPA beads prepared in the sequestration agent) may be added to the same wells of the microtitre plate which is used for treatment of the samples with detergent. Standards may be added to empty microtitre wells on the same plate. Reagents (antisera, tracer and SPA beads) may be added to the same wells as are used for step i) of the process. In the alternative, an aliquot of the plasma or serum sample from step i) may be transferred to individual wells of a second vessel to which are added the immunoassay reagents prepared in sequestrating agent. The plate or assay tubes is incubated for a suitable time period before counting on a β-scintillation counter. The concentration of analyte in the samples is determined by interpolation from a standard curve.

Alternatively, following detergent treatment, a specific binding partner coupled to scintillant beads is incubated with the analyte, together with a second specific binding partner. The second binding partner is unlabelled and detection is through a third binding reagent which is labelled.

Alternatively, following detergent treatment, the antigen/second specific binding partner complex is bound to the scintillant beads, the second specific binding partner being unlabelled and detection is through a third binding reagent which is labelled.

II. Non-radioactive Immunoassay Formats i) Enzyme Immunoassay (EIA)

This approach is based on the competition between unlabelled analyte and a fixed quantity of enzyme-labelled analyte for a limited number of binding sites on an analyte-specific antibody. With fixed amounts of specific antibody and enzyme-labelled analyte, the amount of enzyme-labelled ligand bound by the antibody is inversely proportional to the concentration of added unlabelled ligand. The enzyme-labelled ligand bound to the antibody is immobilised on to polystyrene microtitre wells pre-coated with second antibody. Thus any unbound ligand is removed from the well by simple washing. The amount of enzyme-labelled ligand bound to the antibody is determined with the addition of enzyme substrate.

Plasma or serum samples to be measured are treated with detergent as in step i). Working standards are prepared in buffer containing the detergent. The specific antibody and enzyme conjugate are prepared with assay buffer containing sequestration (cyclodextrin) agent. Standards and pre-treated serum or plasma sample are added to the wells of a second antibody coated microtitre plate. Non-specific binding is measured in the absence of specific antisera. Zero standard consists of assay buffer containing detergent only. Specific antisera and enzyme conjugate (prepared in assay buffer containing cyclodextrin) are pipetted into the wells. Microtitre plates are incubated, followed by thorough washing and addition of enzyme substrate. Optical density is measured and the concentration of analyte in the serum or plasma samples is determined by interpolation from a standard curve.

ii) Enzyme-linked Immunosorbent Assay (ELISA)

This approach employs the quantitative "sandwich" enzyme immunoassay technique. Antibodies specific for the analyte are coated on to the wells of a microtitre plate.

Plasma or serum samples to be measured are treated with detergent as in step i). Working standards are prepared in buffer containing the detergent in a similar manner to the samples. The other components of the ELISA system (e.g. biotinylated antibody, enzyme-labelled specific antibody, streptavidin-labelled enzyme, unlabelled specific antibody and/or enzyme-labelled second antibodies) are added containing the sequestration (cyclodextrin) agent. Optical density is measured and concentration of analyte in the serum or plasma samples is determined by interpolation from a standard curve.

iii) "EMIT" Type (Rubenstein K. E. et al, 1972. Biochem. Biophys. Res. Comm. 47; 846)

The enzymes malate dehydrogenase and glucose-6-phosphate dehydrogenase have been used extensively in the homogeneous immunoassay exemplified by the EMIT (Enzyme Multiplied Immunoassay Technique) system. Both enzymes are monitored by the conversion of the cofactor NAD to $NADH_2$ in a spectrophotometer at 340 nm. In this assay system, the analyte competes with labelled antigen for antibody binding sites. The activity of the enzyme is modified when the antibody binds to the labelled antigen.

Plasma or serum samples to be measured are treated with detergent as in step i), and then the other components of the homogeneous EMIT EIA are added dissolved in buffer containing the sequestration (cyclodextrin) agent. Optical density is measured and the concentration of analyte in the samples is determined by interpolation from a standard curve.

iv) "CEDIA" Type (Henderson D. R. et al 1986 Clin. Chem. 32, 1637–1641)

In the cloned enzyme donor immunoassay method, two inactive fragments of β-galactosidase have been synthesized by genetic engineering. The large fragment, the enzyme acceptor, contains 95% of the enzyme, and the small fragment, the enzyme donor, consists of the remaining 5%. On mixing, the two fragments aggregate into tetramers which have β-galactosidase enzyme activity. In this assay, antigen is conjugated to the enzyme donor in such a way that aggregation with the enzyme acceptor is blocked if antibody binds to antigen. In the presence of analyte, less conjugate is bound by antibody, and enzyme activity is stimulated. In the absence of analyte, antibody binding to the conjugate prevents formation of the active enzyme.

Plasma or serum samples to be measured are treated with detergent as in step i), and then the other components of the homogeneous CEDIA (antibody, enzyme-donor/ligand conjugate, enzyme acceptor monomer) are added dissolved in buffer containing the sequestration (cyclodextrin) agent. Optical density is measured and the concentration of analyte in the samples is determined by interpolation from a standard curve.

v) Separation-based Fluorescence Immunoassays

As with other labels the use of fluorophores gives rise to a number of different immunoassay methods which can be divided into the basic categories of fluorescence immunoassay (FIA; with limited reagent, labelled antigen) and immunofluorometric assay (IFMA; excess reagent, labelled antibody). Fundamentally, FIAs and IFMAs are identical to other immunoassays, such as EIAs and ELISAs, except a fluorophore (e.g. a cyanine dye, rhodamine or fluorescein) is used as a label.

In these assays plasma or serum samples to be measured are treated with detergent as in step i). Working standards are prepared in buffer containing the detergent in a similar manner to the samples. The other key components of the assay system are added prepared in buffer containing the sequestration (cyclodextrin) agent. Fluorescence intensity is measured and the concentration of analyte in the samples is determined by interpolation from a standard curve.

vi) Homogeneous Fluorescence Immunoassays a) Fluorescence Polarization

Fluorescence polarization is a technique used to distinguish from free analyte without the need for separation. In competitive assays, for small molecules, fluorescent-labelled antigens (e.g. using fluorescein, rhodamine or cyanine dye reagents) as tracer. At the signal generation and detection stage, a fluorimeter generates vertically polarized light at the excitation wavelength of the fluorophore.

The emitted light, at a lower wavelength because of Stokes' shift, is detected through a vertical polarizing filter. Because free tracer rotates at a very high speed, the emitted light is always in a different plane from the incident light, so the amount of light detected through the polarizing filter is minimal. However the tracer bound the much larger antibody molecule is restrained from rotating at such a high speed and the emitted light is in almost the same plane as the incident light. Plasma or serum samples to be measured are treated with detergent as in step i), and then the other components of the homogeneous fluorescence assay (antibody, fluorescent-tagged antigen) are added dissolved in buffer containing the sequestration (cyclodextrin) agent. Fluorescence is measured and the concentration of analyte in the samples is determined by interpolation from a standard curve.

b) Fluorescence Resonance Energy Transfer (FRET)

Different fluorophores often have different activation and emission spectra (see Table 1). However, the activation peak of one fluorophore may overlap with the emission peak of another fluorophore. This principle may be applied for homogeneous assays in one or two ways, dependent on the properties of the second fluorophore. If the second fluorophore is placed in the immediate vicinity of the first, quenching of the fluorescent emission takes place through transfer of energy. This principle has been used in FRET by coupling one fluorophore to antibody and another to antigen. Binding of the antigen to antibody leads to close proximity and subsequent quenching. An alternative system involves two populations of antibodies raised against the same antigen, labelled with two different fluorophores. Binding of the two antibodies gives rise to close proximity and thus energy transfer between the two leading to quenching or reduction in fluorescence. The second fluorophore may act as an energy transfer acceptor and emit at a higher wavelength, than the donor fluorophore, instead of acting as a quencher. Thus determination of the emission at the higher wavelength reflects the level of binding of labelled antigen to antibody in competitive assays, or labelled antibodies in a sandwich assay. Plasma or serum samples to be measured are treated with detergent as in step i), and then the other components of the homogeneous fluorescence energy transfer assay are added dissolved in buffer containing the sequestration (cyclodextrin) agent. Fluorescence is measured and the concentration of analyte in the samples is determined by interpolation from a standard curve.

TABLE 1

The Spectral Properties of Cyanine Fluorescent Dyes

| Fluorophore | Activation (nm) | Emission (nm) |
|---|---|---|
| Cy2 | 489 | 506 |
| Cy3 | 550 | 570 |
| Cy3.5 | 581 | 596 |
| Cy5 | 649 | 670 |
| Cy5.5 | 675 | 694 |
| Cy7 | 743 | 767 |
| FluorX | 494 | 520 | c) Time-resolved Fluorescence

Background fluorescence is one of the main problems with the use of fluorescence immunoassay, and its presence can severely limit the use of these methods. However, background fluorescence present in most biological material has the short lifetime of a few nanoseconds. For fluorophores with long fluorescence lifetimes, it is possible to measure fluorescence at a time when virtually all the background fluorescence has disappeared. This is essentially the principle of time resolved fluorescence and this method can be used in combination with fluorescence energy transfer and fluorescence polarization techniques.

III. Other Methods

The method described in this patent can be applied to other immunoassay techniques such as chemiluminescence, nephelometry, latex agglutination assays and their variants.

EXAMPLES

1. System Optimisation

Measurement of interleukin-6 (IL-6) was selected as a model system for studying dissociation from soluble receptors and measurement of total cytokine in plasma. Detergents were used in a series of preliminary experiments in combination with sequestrating reagent in order to determine optimal concentration. Dose-response curves for IL-6 were prepared in detergent and cyclodextrin. Parameters such as assay sensitivity, working range and antigen: antibody binding were used to establish the most suitable reagents and optimal concentrations for both detergent and cyclodextrin.

Reagents, Buffers and Equipment
Human Interleukin-6 ELISA kit, Amersham, RPN 2754
Alpha-cyclodextrin, USB, 13979
Dodecyltrimethylammonium bromide (DTAB), Sigma, D8638
Disposable test tubes for preparing working standards
Pipettes and pipetting equipment
Laboratory glassware
Distilled water
Magnetic stirrer
Microtitre plate washer
Microtitre plate reader Method Standard curves were prepared as follows. Working standards (10.24–400 pg/ml IL-6) were prepared in polypropylene tubes with assay buffer containing 1% (w/v) DTAB. The biotinylated antibody was prepared in buffer containing 3% (w/v) alpha-cyclodextrin. 50 µl of biotinylated antibody reagent (containing cyclodextrin) was added to the anti-IL-6 coated plate. 50 µl of working standard was pipetted into wells of the anti-IL-6 coated plate. Non-specific binding was determined in the absence of IL-6 (zero IL-6 standard). The order of addition of biotinylated antibody and standards is not critical to the procedure. However, in all examples, improved results were obtained when the biotinylated antibody was added to the anti-IL-6 coated plate before the standards. The anti-IL-6 plate, containing biotinylated antibody and standards was incubated for 2 hours at room temperature. The plate was washed thoroughly, followed by the addition of 100 µl/well of diluted (30 µl of concentrate to 12 ml of streptavidin dilution buffer) peroxidase-labelled streptavidin. The plate was incubated at room temperature for 30 minutes followed by thorough washing. 100 µl of TMB substrate was added to each well of the plate, followed by a 30 minute incubation at room temperature. The reaction was terminated by the addition of 100 µl/well sulphuric acid. The optical density was determined with a microtitre plate spectrophotometer.

Comparisons were made with curves prepared with assay buffer containing:
  Standards and antibodies in assay buffer only (DTAB and cyclodextrin absent)
  Standards prepared in DTAB, antibodies prepared in assay buffer only.

Results

Figure 1:
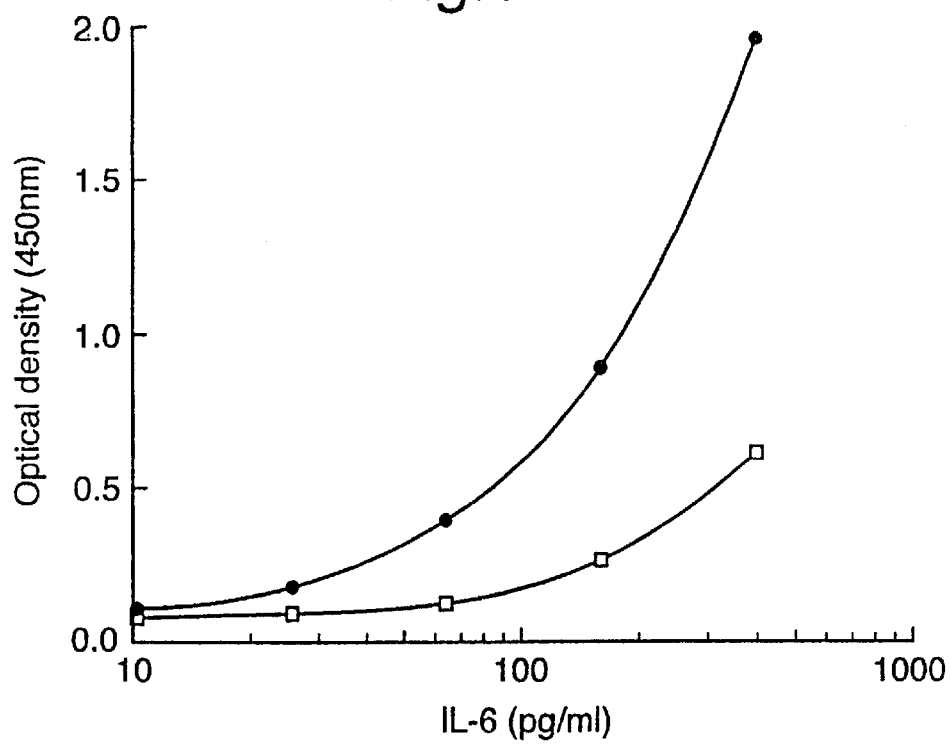

The effect of including detergent and sequestrant on the IL-6 ELISA system is presented in FIGS. 1 & 2. FIG. 1 shows an inhibition of antibody binding when 1% (w/v) DTAB is added to the IL-6 assay. Binding was restored upon inclusion of 3% (w/v) alpha-cyclodextrin to the biotinylated anti-IL-6 antibody.

2. Measurement of Total Interleukin-6 in Plasma

This experiment describes a simple method for the measurement of total cytokine in plasma. The technique described here is a two-step method where a detergent is added to plasma and an aliquot is subsequently removed for measurement using an immunoassay (ELISA) technique. The critical component of the ELISA (the biotinylated antibody) was prepared in buffer containing cyclodextrin.

Reagents, Buffers and Eguipment

Human Interleukin-6 ELISA kit, Amersham, RPN 2754
Normal human plasma
Alpha-cyclodextrin, USB, 13979
Dodecyltrimethylammonium bromide (DTAB), Sigma, D8638
Disposable test tubes for preparing working standards
Pipettes and pipetting equipment
Laboratory glassware
Distilled water
Magnetic stirrer
Microtitre plate washer
Microtitre plate reader Method Detergent (DTAB) was added to plasma or serum to give a final concentration of 1% (w/v). Typically 100 µl of 10% (w/v) DTAB in assay buffer was added to 900 µl of serum or plasma sample. An aliquot (50 µl) of the treated serum or plasma was removed for assay. IL-6 standards were prepared with assay buffer containing 1% (w/v) DTAB.

Working standards (10.24–400 pg/ml IL-6) were prepared in polypropylene tubes with assay buffer containing 1% (w/v) DTAB. The biotinylated antibody was prepared in buffer containing 3% (w/v) alpha-cyclodextrin. 50 µl of biotinylated antibody reagent (containing cyclodextrin) was added to the anti-IL-6 coated plate. 50 µl of working standard and pre-treated serum or plasma sample were pipetted into separate wells of the anti-IL-6 coated plate. Non-specific binding was determined in the absence of IL-6. The anti-IL-6 plate, containing biotinylated antibody and standards/samples was incubated for 2 hours at room temperature. The plate was washed thoroughly, followed by the addition of 100 µl/well of diluted (30 µl of concentrate to 12 ml of streptavidin dilution buffer) peroxidase-labelled streptavidin. The plate was incubated at room temperature for 30 minutes followed by thorough washing. 100 µl of TMB substrate was added to each well of the plate, followed by a 30 minute incubation at room temperature. The reaction was terminated by the addition of 100 µl/well sulphuric acid. The optical density was determined with a microtitre plate spectrophotometer. Il-6 levels were determined using log/linear analysis with reference to a standard curve. Levels of cytokine in serum or plasma were determined by interpolation.

Results

The effects of adding detergent to normal human plasma samples, and, cyclodextrin to the key reagents of the IL-6 ELISA system are shown in Table 2. Plasma samples were diluted with assay buffer (neat plasma and diluted 1:5–1:20) before measurement. Control samples were prepared in the absence of detergent and measured without the addition of cyclodextrin to the biotinylated antibodies. Samples treated with detergent and measured in the presence of cyclodextrin exhibited a significant increase in IL-6 concentration (a mean rise of 165%). This unexpected observation is considered to be the result of dissociation of plasma IL-6 from naturally occurring, soluble IL-6 receptor.

TABLE 2

Measurement of IL-6 in plasma

| Sample dilution | Control (pg/ml) | Samples plus detergent Antibodies plus cyclodextrin (pg/ml) |
|---|---|---|
| Neat plasma | 3.5 | 8.9 |
| 1:5 | 4.1 | 7.6 |
| 1:10 | 3.6 | 7.6 |
| 1:20 | 1.6 | 9.8 |

3. Recovery of Known Amounts of Added Interleukin-6 From Plasma Samples

In order to confirm the utility of the method, recovery experiments were carried out with known quantities of IL-6 added to normal human plasma. Samples were measured in the presence and absence of detergent and cyclodextrin. A range of concentrations of IL-6 and dilutions of plasma were evaluated.

Reagents, Buffers and Equipment
Human Interleukin-6 ELISA kit, Amersham, RPN 2754
Normal human plasma
Recombinant human interleukin-6, Amersham, ARM 20010
Alpha-cyclodextrin, USB, 13979
Dodecyltrimethylammonium bromide (DTAB), Sigma, D8638
Disposable test tubes for preparing working standards
Pipettes and pipetting equipment
Laboratory glassware
Distilled water
Magnetic stirrer
Microtitre plate washer
Microtitre plate reader Method Recombinant IL-6 was added to normal human plasma at a range of concentrations (25–200 pg/ml). Several different dilutions (neat plasma, 1:5–1:20) of plasma were spiked with IL-6. Detergent (DTAB) was added to plasma to give a final concentration of 1% (w/v). Typically 100 µl of 10% (w/v) DTAB prepared in assay buffer was added to 900 µl of plasma sample. An aliquot (50 µl) of the treated plasma was removed for assay. IL-6 standards were prepared with assay buffer containing 1% (w/v) DTAB.

Working standards (10.24–400 pg/ml IL-6) were prepared in polypropylene tubes with assay buffer containing 1% (w/v) DTAB. The biotinylated antibody was prepared in buffer containing 3% (w/v) alpha-cyclodextrin. 50 µl of biotinylated antibody reagent(containing cyclodextrin) was added to the anti-IL-6 coated plate. 50 µl of working standard and pre-treated plasma sample were pipetted into separate wells of the anti-IL-6 coated plate. Non-specific binding was determined in the absence of IL-6. The anti-IL-6 plate, containing biotinylated antibody and standards/samples was incubated for 2 hours at room temperature. The plate was washed thoroughly, followed by the addition of 100 µl/well of diluted (30 µl of concentrate to 12 ml of streptavidin dilution buffer) peroxidase-labelled streptavidin. The plate was incubated at room temperature for 30 minutes followed by thorough washing. 100 µl of TMB substrate was added to each well of the plate, followed by a 30 minute incubation at room temperature. The reaction was terminated by the addition of 100 µl/well sulphuric acid. The optical density was determined with a microtitre plate spectrophotometer. Interleukin-6 levels were determined using log/linear analysis with reference to a standard curve. Levels of cytokine in plasma were determined by interpolation. Control samples were prepared in the absence of detergent and measured without the addition of cyclodextrin to the biotinylated antibodies.

Results

The effect of adding detergent to normal human plasma samples spiked with known concentrations of recombinant IL-6 is shown in FIG. 3. The recovery of IL-6 measured in the absence of detergent and cyclodextrin was relatively low (mean recovery 63%). Samples treated with detergent and measured in the presence of cyclodextrin exhibited an increase in recovery of added IL-6 (mean recovery 93%). This unexpected observation is considered to be the result of dissociation of plasma IL-6 from naturally occurring, soluble IL-6 receptor.

4. Effect of Adding Soluble Interleukin-6 Receptor to Plasma Samples

Recovery experiments were carried out with known quantities of IL-6 and soluble receptor added to normal human plasma. Samples were measured both in the presence and absence of detergent and cyclodextrin. A range of concentrations of IL-6 and dilutions of plasma were evaluated.

Reagents, Buffers and Equipment
Human Interleukin-6 ELISA kit, Amersham, RPN 2754
Normal human plasma
Recombinant human interleukin-6, Amersham, ARM 20010
Recombinant human IL-6 soluble receptor, R&D Systems, 227SR-025
Alpha-cyclodextrin, USB, 13979
Dodecyltrimethylammonium bromide (DTAB), Sigma, D8638
Disposable test tubes for preparing working standards
Pipettes and pipetting equipment
Laboratory glassware
Distilled water
Magnetic stirrer
Microtitre plate washer
Microtitre plate reader Method Recombinant IL-6 was added to normal human plasma at a range of concentrations (25–200 pg/ml) in the presence of 12.5 ng/ml soluble IL-6 receptor. Several different dilutions (neat plasma, 1:5–1:20) of plasma were spiked with IL-6. Detergent (DTAB) was added to plasma to give a final concentration of 1% (w/v). Typically 100 µl of 10% (w/v) DTAB prepared in assay buffer was added to 900 µl of plasma sample. An aliquot (50 µl) of the treated plasma was removed for assay. IL-6 standards were prepared with assay buffer containing 1% (w/v) DTAB. Working standards (10.24–400 pg/ml IL-6) were prepared in polypropylene tubes with assay buffer containing 1% (w/v) DTAB. The biotinylated antibody was prepared in buffer containing 3% (w/v) alpha-cyclodextrin. 50 µl of biotinylated antibody reagent (containing cyclodextrin) was added to the anti-IL-6 coated plate. 50 µl of working standard and pre-treated plasma sample Were pipetted into separate wells of the anti-IL-6 coated plate. Non-specific binding was determined in the absence of IL-6. The anti-IL-6 plate, containing biotinylated antibody and standards/samples was incubated for 2 hours at room temperature. The plate was washed thoroughly, followed by the addition of 100 µl/well of diluted (30 µl of concentrate to 12 ml of streptavidin dilution buffer) peroxidase-labelled streptavidin. The plate was incubated at room temperature for 30 minutes followed by thorough washing. 100 µl of TMB substrate was added to each well of the plate, followed by a 30 minute incubation at room temperature. The reaction was terminated by the addition of 100 µl/well sulphuric acid. The optical density was determined with a microtitre plate spectrophotometer. Interleukin-6 levels were determined using log/linear analysis with reference to a standard curve. Levels of cytokine in plasma were determined by interpolation. Control samples were prepared in the absence of detergent and measured without the addition of cyclodextrin to the biotinylated antibodies.

Results

The effects of adding detergent to normal human plasma samples spiked with known concentrations of recombinant IL-6 and 12.5 mg/ml soluble IL-6 receptor are shown in FIG. 4. The recovery of IL-6 measured in the absence of detergent and cyclodextrin was relatively low (mean recovery 22%). Samples treated with detergent and measured in the presence of cyclodextrin exhibited an increase in recovery of added IL-6 (mean recovery 47%). Clearly, the increase in recovery is the direct result of dissociation of plasma IL-6 from the recombinant IL-6 receptor.

5. Direct Measurement of Prostaglandin $E_2$ in Plasma

This experiment describes a simple method for the direct measurement of prostaglandin $E_2$ ($PGE_2$) in plasma. According to the method, detergent is added to plasma and an aliquot is subsequently removed for measurement using a competitive enzyme immunoassay (EIA). The critical components of the assay (the antisera and $PGE_2$ conjugate) were prepared in buffer containing cyclodextrin.

Reagents and Equipment
Prostaglandin $E_2$ EIA kit, Amersham Pharmacia Biotech, RPN 222
Normal human plasma (prepared in the presence of indomethacin- see below)
Alpha-cyclodextrin, USB, 13979
Dodecyltrimethylammonium bromide (DTAB), Sigma, D8638
Disposable test tubes for preparing working standards
Pipettes and pipetting equipment
Laboratory glassware
Distilled water
Magnetic stirrer
Microtitre plate washer
Microtitre plate reader Method All plasma samples were processed immediately after collection and assayed as soon as possible. Levels of $PGE_2$ in plasma decrease significantly if stored at −15° C. to −30° C. for one week. EDTA or citrate are recommended as anticoagulants. 2 g of disodium EDTA and 0.8 g NaCl were added to water, the pH adjusted with 1M NaOH to 7.4, and, the final volume made up to 100 ml with distilled water. 50 mg indomethacin was added to 3.5 ml absolute ethanol. For each blood collection tube, 0.25 ml EDTA solution was added to 0.05 ml of indomethacin. 10 ml of fresh blood was added to each tube, the sample centrifuged immediately at 15000×g for 15 minutes at 4° C., the upper plasma layer removed and rapidly frozen. The samples were stored at −15° C. to −30° C.

Detergent (DTAB) was added to plasma to give a final concentration of 0.25% (w/v). Typically 100 µl of 2.5% (w/v) DTAB, prepared in $PGE_2$ EIA kit assay buffer, were added to 900 µl of plasma sample. An aliquot (50 µl) of the treated plasma was removed for assay. $PGE_2$ standards were prepared with assay buffer containing 0.25% (w/v) DTAB.

Working PGE$_2$ standards (2.5–320 pg/well) were prepared in polypropylene tubes with assay buffer containing 0.25% (w/v) DTAB. The PGE$_2$ antibody and PGE$_2$ conjugate were prepared with assay buffer containing 1.5% (w/v) alpha-cyclodextrin. 50 µl of working standard and DTAB-treated plasma sample were pipetted into separate wells of a goat anti-mouse IgG coated plate. Non-specific binding was measured in the absence of PGE$_2$ antisera. Zero standard PGE$_2$ consisted of assay buffer containing 0.25% (w/v) DTAB only. 50 µl of antisera and 50 µl conjugate (prepared in assay buffer containing 1.5% (w/v) alpha-cyclodextrin) were pipetted into the appropriate test wells (containing standards or treated plasma samples). The plates were incubated for 1 hour at room temperature with constant shaking, followed by thorough washing. 150 µl of TMB substrate was added to all wells and incubated for 30 minutes at room temperature. The reaction was terminated by the addition of 100 µl/well sulphuric acid. The optical densities were determined with a microtitre plate spectrophotometer set at 450 nm. Intracellular PGE$_2$ levels were determined using log/linear analysis with reference to a standard curve. Levels were estimated by interpolation.

Results

The effects of adding detergent to plasma samples, and, cyclodextrin to the key reagents of the PGE$_2$ EIA system are shown in Table 3. Control samples were prepared in the absence of detergent and measured without the addition of cyclodextrin to antisera and conjugate. Plasma samples treated with detergent and measured in the presence of cyclodextrin exibited a significant increase in PGE$_2$ concentration (mean rise of 215%). This unexpected observation is considered to be result dissociation of PGE$_2$ from a naturally occurring, soluble PGE$_2$ receptor.

TABLE 3

Measurement of PGE$_2$ in plasma

| Sample | Control (pg/well) | Plasma samples treated with detergent. Antisera and conjugate prepared in cyclodextrin. (pg/well) |
| --- | --- | --- |
| 1 | 5.7 | 18.0 |
| 2 | 11.5 | 23.5 |
| 3 | 9.1 | 20.0 |
| 4 | 7.4 | 35.0 |
| 5 | 8.9 | 38.0 |

6. Recovery of Known Amounts of Added Prostaglandin E$_2$ from Plasma Samples

Plasma samples were prepared in the presence of indomethacin as described in Example 5. A range of concentrations of PGE$_2$ and dilutions of plasma were evaluated.

Reagents and Equipment

Prostaglandin E$_2$ EIA kit, Amersham Pharmacia Biotech, RPN 222 Normal human plasma (prepared in the presence of indomethacin)
Alpha-cyclodextrin, USB, 13979
Dodecyltrimethylammonium bromide (DTAB), Sigma, D8638
Disposable test tubes for preparing working standards
Pipettes and pipetting equipment
Laboratory glassware
Distilled water
Magnetic stirrer
Microtitre plate washer
Microtitre plate reader Method PGE$_2$ was added to human plasma over a range of concentrations (25–200 pg/ml). Several different dilutions (neat plasma, 1:5–1:20) of plasma were spiked with PGE$_2$. Typically 100 µl of 2.5% (w/v) DTAB, prepared in PGE$_2$ EIA kit assay buffer, were added to 900 µl of plasma sample. An aliquot (50 µl) of the treated plasma was removed for assay. PGE$_2$ standards were prepared with assay buffer containing 0.25% (w/v) DTAB. Working PGE$_2$ standards (2.5–320 pg/well) were prepared in polypropylene tubes with assay buffer containing 0.25% (w/v) DTAB. The PGE$_2$ antibody and PGE$_2$ conjugate were prepared with assay buffer containing 1.5% (w/v) alpha-cyclodextrin. 50 µl of working standard and DTAB-treated plasma sample were pipetted into separate wells of a goat anti-mouse IgG coated plate. Non-specific binding was measured in the absence of PGE$_2$ antisera. Zero standard PGE$_2$ consisted of assay buffer containing 0.25% (w/v) DTAB only. 50 µl of antisera and 50 µl conjugate (prepared in assay buffer containing 1.5% (w/v) alpha-cyclodextrin) were pipetted into the appropriate test wells (containing standards or treated plasma samples). The plates were incubated for 1 hour at room temperature with constant shaking, followed by thorough washing. 150 µl of TMB substrate was added to all wells and incubated for 30 minutes at room temperature. The reaction was terminated by the addition of 100 µl/well sulphuric acid. The optical densities were determined with a microtitre plate spectrophotometer set at 450 nm. Intracellular PGE$_2$ levels were determined using log/linear analysis with reference to a standard curve. Levels were estimated by interpolation. Control samples were prepared in the absence of detergent and measured without the addition of cyclodextrin to the antisera and conjugate.

Results

The effect of adding detergent to normal human plasma samples spiked with known concentration of PGE$_2$ is shown in FIG. 5. The recovery of PGE$_2$ measured in the absence of detergent and cyclodextrin was relatively low (mean recovery 63%). Samples treated with detergent and measured in the presence of cyclodextrin exhibited an increase in recovery of added PGE$_2$ (mean recovery 103%). This unexpected observation is considered to be result dissociation of PGE$_2$ from a naturally occurring, soluble PGE$_2$ receptor.

LEGENDS TO THE FIGURES

FIG. 1. Inhibition of Binding in the IL-6 ELISA With Detergent

Interleukin-6 standards (10.24–400 pg/ml) were prepared in standard diluent either in the presence (□) or absence (●) of detergent (1% w/v DTAB). Aliquots (50 µl) of biotinylated antibody (zero cyclodextrin) were added to the anti-IL-6 coated plate followed by standard (50 µl). The plate was incubated for 2 hours at room temperature, and the optical density measured as described under the methods section.

FIG. 2. Restoration of Binding in the IL-6 ELISA With Cyclodextrin

Interleukin-6 (10.24–400 pg/ml) were prepared in standard diluent either in the presence (□) or absence (●) of detergent (1% DTAB). Aliquots (50 µl) of biotinylated antibody, prepared in the presence (□) or absence (●) of cyclodextrin (3% w/v), were added to the anti-IL-6 coated plate followed by standard (50 µl). The plate was incubated for 2 hours at room temperature, and the optical density measured as described under the methods section.

FIG. 3. Recovery of Recombinant Interleukin-6 From Plasma

Normal human plasma samples were spiked with known concentrations (25–200 pg/ml) of recombinant human interleukin-6. Samples were measured in the presence (A) and absence (B) of detergent and cyclodextrin. A number of different dilutions of plasma were evaluated. Assays were carried out as described under the methods section.

FIG. 4. Recovery of Recombinant Interleukin-6 From Plasma in the Presence of Soluble IL-6 Receptor Normal human plasma samples were spiked with known concentrations (25–200 pg/ml) of recombinant human interleukin-6 and soluble IL-6 receptor (12.5 ng/ml). Samples were measured in the presence (A) and absence (B) of detergent and cyclodextrin. A number of different dilutions of plasma were evaluated. Assays were carried out as described under the methods section.

FIG. 5. Recovery of $PGE_2$ From Plasma

Normal human plasma samples were spiked with known concentrations (25–200 pg/ml) of $PGE_2$. Samples were measured in the presence (A) and absence (B) of detergent and cyclodextrin. A number of different dilutions of plasma were evaluated. assays were carried out as described in the Methods section.]

What is claimed is:

1. A method of assaying for an analyte which occurs at least partially bound as a complex with its soluble receptor or binding protein, said method comprising the steps of:
   i) forming a fluid mixture by mixing a biological fluid sample containing said analyte with a detergent, said detergent dissociating said complex, in said biological fluid sample;
   ii) mixing said fluid mixture with reagents and with a sequestrant for said detergent, wherein said reagents include a specific binding partner of said analyte, and said binding partner binding thereto;
   iii) performing a specific binding assay for said analyte in said fluid mixture containing said sequestrant.

2. The method of claim 1, wherein said sequestrant is a cyclodextrin.

3. The method of claim 2, wherein said sequestrant is present in an amount of about 1–5% of said fluid mixture containing said sequestrant.

4. The method of claim 1, wherein said forming, mixing, and performing steps are all performed in a single reaction vessel.

5. The method of claim 1, wherein said performing step further comprises:
   providing one of a multiwell plate or a plurality of assay tubes; and
   performing multiple assays in parallel in one of said multiwell plate or said assay tubes.

6. The method of claim 1, wherein said assay of said performing step is a homogenous assay.

7. The method of claim 6, wherein said assay of said performing step is a scintillation proximity assay.

8. The method of claim 1, wherein said specific binding assay of said performing step is an immunoassay.

9. The method of claim 1, wherein said analyte is selected from the group consisting of interleukin-6 and prostaglandin $E_2$, said detergent is dodecyl trimethyl ammonium bromide, and said sequestrant is α-cyclodextrin.

* * * * *